US006284493B1

(12) United States Patent
Roth

(10) Patent No.: US 6,284,493 B1
(45) Date of Patent: Sep. 4, 2001

(54) METHOD OF SYNTHESIZING SACCHARIDE COMPOSITIONS

(75) Inventor: Stephen Roth, Gladwyne, PA (US)

(73) Assignee: Neose Technologies, Inc., Horsham, PA (US)

( * ) Notice: Subject to any disclaimer, the term of this patent is extended or adjusted under 35 U.S.C. 154(b) by 0 days.

(21) Appl. No.: 09/265,067

(22) Filed: Mar. 9, 1999

Related U.S. Application Data

(63) Continuation of application No. 08/664,882, filed on Jun. 17, 1996, now Pat. No. 5,879,912, which is a continuation of application No. 08/091,372, filed on Jul. 15, 1993, now abandoned.

(51) Int. Cl.$^7$ .................................................... C12P 19/00
(52) U.S. Cl. ...................... 435/72; 435/252.33; 435/193; 536/23.2
(58) Field of Search ................................ 435/72, 252.33, 435/289.1, 193; 536/23.2, 23.1

(56) References Cited

U.S. PATENT DOCUMENTS

| 4,590,160 | 5/1986 | Nishihashi ............................. 435/78 |
| 5,032,519 | 7/1991 | Paulson et al ....................... 435/193 |
| 5,047,335 | 9/1991 | Paulson et al. ..................... 435/69.1 |
| 5,135,854 | 8/1992 | Mackay et al. ..................... 435/69.1 |
| 5,141,858 | 8/1992 | Paul et al. ............................. 435/97 |
| 5,149,640 | 9/1992 | Oonishi et al. ...................... 435/100 |
| 5,180,674 | 1/1993 | Roth .................................. 435/293.1 |
| 5,324,663 | 6/1994 | Lowe ................................. 435/320.1 |
| 5,348,867 | 9/1994 | Georgiou et al. ................... 435/69.7 |
| 5,545,553 | 8/1996 | Gotschlich ...................... 435/252.33 |

FOREIGN PATENT DOCUMENTS 0 325 872    8/1989   (EP) .

OTHER PUBLICATIONS

Paulson et al. Glycosyltransferases. Structure, localization, and control of cell type–specificglycosylation. J. Biol Chem. Oct. 25, 1989, vol. 264, pp. 17615–8.*

Agterberg et al., 1990, "Outer Membrane of PhoE Protein of *Escherichia coli* K–12 as an Exposure Vector: Possibilities and Limitations", Gene 88:37–45.

Aoki et al., 1992, "Golgi Retention of a Trans–Golgi Membrane Protein, Galactosyltransferase", Proc. Natl. Acad. Sci USA 89:4319–4323.

Charbit et al., 1988, "Versatility of a Vector for Expressing Foreign Polypeptides at the Surface of Gram–Negative Bacteria", Gene 70:181–189.

Charbit et al., 1986, "Probing the Topology of a Bacterial Membrane Protein by Genetic Insertion of a Foreign Epitope: Expression at the Cell Surface", EMBO J. 5:3029–3037.

Creeger et al., 1982, "Cloning Genes for Bacterial Glycosyltransferases", Complex Carbohydrates, Part D, Meth. Enzymol. 83:326–331.

Evans et al., 1993, "Dominant Negative Mutation in Cell Surface β 1,4–Galactosyltransferase Inhibits Cell–Cell and Cell–Matrix Interactions", J. Cell. Biol. 120:1045–1057.

Francisco et al., 1992, "Transport and Anchoring of β–Lactamase to the External Surface of *Escherichia coli*", Proc. Natl. Acad. Sci. USA 89:2713–2717.

Freudl et al., 1989, "Insertion of Peptides into Cell Surface Exposed Areas of the *Escherichia coli* OmpA Protein Does Not Interfere with Export and Membrane Assembly", Gene 82:229–236.

Ghrayeb et al., 1984, "Nine Amino Acid Residues at the $NH_2$ Terminal of Lipoprotein are Sufficient for Its Modification, Processing and Localization in the Outer Membrane of *Escherichia coli*", J. Biol. Chem. 259:463–467.

Kadam et al., 1985, "Cloning of rfaG, B, I and J Genes for Glycosyltransferase Enzymes for Synthesis of the Lipopolysaccharide Core of *Salmonella typhimurium*", J. Bacteriol. 161:277–284.

Kojima et al., 1987, "Predefined Gene Transfer for Expression of a Glycosphingolipid Antigen by Transfection with a Cosmid Genomic Library Peptide from a Cell Line in which the Specific Glycosphingolipid is Highly Expressed", Biochem. Biophys. Res. Comm. 143:716–722.

LaMont et al., 1977, "Cell–Surface Glycosyltransferases in Cultured Fibroblasts: Increased Activity and Release During Serum Stimulation of Growth", Proc. Natl. Acad. Sci. USA 74:1086–1090.

Larsen et al., 1990, "Molecular Cloning Sequence and Expression of a Human GDP–L–Fucose–β–D–Galactoside 2–α–L–Fucosyltransferase cDNA", Proc. Natl. Acad. Sci. USA 87:6674–6678.

Larsen et al., 1989, "Isolation of a cDNA Encoding a Murine UDP Galactose: β–D–Galactosyl–1, 4–N Acetyl D–Glucosaminide α–1,3–Galactosyltransferase Expression Cloning in Gene Transfer", Proc. Natl. Acad. Sci. USA 86:8227–8231.

Lowe et al., 1991, "Molecular Cloning of a Human Fucosyltransferase Gene that Determines Expression of the Lewis X and VIM–2 Epitopes but not ELAM–1 Dependent Cell Adhesion", J. Biol. Chem. 266:17467–17477.

Mukasa et al., 1989, "Purification and Characterization of Cell–Associated Glucosyltransferase Synthesizing Insoluble Glucan from *Streptococcus mutans* Serotype C", J. Gen. Microbiol. 135:2055–2063.

(List continued on next page.)

*Primary Examiner*—Nashaat T. Nashed
*Assistant Examiner*—Christian L. Fronda
(74) *Attorney, Agent, or Firm*—Pennie & Edmomds LLP

(57) ABSTRACT

A method of synthesizing saccharide compositions is described. In this method, an acceptor moiety is contacted with at least one donor saccharide in the presence of at least one cell surface-bound glycosyltransferase specific for catalyzing the coupling of the acceptor moiety with the donor saccharide. The acceptor moiety used is a carbohydrate, a protein, a lipid, or a glycolipid.

28 Claims, No Drawings-

OTHER PUBLICATIONS

Patt et al., 1975, "Ectoglycosyltransferase Activity in Suspensions and Monolayers of Cultured Fibroblasts", Biochem. Biophys. Res. Commun. 67:483–490.

Patt et al., 1974, "Cell Surface Glycolipid and Glycoprotein Glycosyltransferases", J. Biol. Chem. 249:4157–4165.

Paulson et al., 1989, "Glycosyltransferases. Structure, Localization and Control of Cell Type Specific Glycosylation", J. Biol. Chem. 264:17615–17618.

Pierce et al., 1980, "Cell Surface Glycosyltransferase Activities", Intl. Rev. Cytol. 65:1–47.

Rawn, 1989, *Biochemistry,* Neil Patterson, Pub., NC, pp. 548–554; 878–882.

Roth, 1990, "Glycosyltransferases as Effectors of Cell Recognition", Ch. 5 In: *Molecular Analyses of Supracellular Phenomena,* Penn Press Series in Developmental Biology, Roth, ed., Univ. of Pennsylvania Press, pp. 201–223.

Teasdale et al., 1992, "The Signal for Golgi Retention of Bovine β–1,4–Galactosyltransferase is in the Transmembrane Domain", J. Biol. Chem. 267:4084–4096.

Thiry et al., 1989, "Cloning of DNA Sequences Encoding Foreign Peptides and their Expression in the K88 Pili", Appl. and Environ. Microbiol. 55:984–993.

Weiser et al., 1973, "Intestinal Epithelial Cell Surface Membrane Glycoprotein", J. Biol. Chem. 248:2542–2548.

Yamamoto et al., 1980, "Cloning and Characterization of DNA Complementary to Human UDP–GalNAc: Fuc α1–2 Gal α 1,3–GalNAc Transferase", J. Biol. Chem. 265:1146–1151.

Yogeeswaran et al., 1974, "Mechanism of Cell Contact–Dependent Glycolipid Synthesis: Further Studies with Glycolipid–Glass Complex", Biochem. Biophys. Res. Comm. 59:591–599.

Bierhuizen and Fukuda, 1992, "Expression cloning of a cDNA encoding UDP–GlcNac:Galβ1–3–GalNAc–R (GlcNAc to GalNAc) β1–6GlcNAc transferase by gene transfer into CHO cells expressing polyoma large tumor antigen", Proc. Natl. Acad. Sci. USA 89:9326–9330.

Burchell et al., 1991, "The UDP glucuronosyltransferase gene superfamily: suggested nomenclature based on evolutionary divergence", DNA and Cell Biol. 10:487–494.

Clausen et al., 1992, "Carbohydrates of the cell surface: molecular aspects of the glycosyltransferases and their genes", APMIS Suppl 27:9–17.

Colley et al., 1989, "Conversion of a Golgi apparatus sialyltransferase to a secretory protein by replacement of the $NH_2$–terminal signal anchor with a signal peptide", J. Biol. Chem. 264:17619–17622.

D'Agostaro et al., 1989, "Cloning of cDNA encoding the membrane–bound form of bovine β1,4–galactosyltansferase", Eur. J. Biochem. 183:211–217.

Ernst et al., 1989, "Stable expression of blood group H determinants and GDP–L–fucose: β–D–galactoside 2–α–L–fucosyltransferase in mouse cells after transfection with human DNA", J. Biol. Chem. 264:3436–3447.

Homa et al., 1993, "Isolation and expression of a cDNA clone encoding a bovine UDP–GalNAc:polypeptide N–acetlygalactosaminyltransferase", J. Biol. Chem. 268:12609–12616.

Jackson et al., 1987, "Cloning of a human liver microsomal UDP–glucuronosyltransferase cDNA", Biochem. J. 242:581–588.

Jackson and Burchell, 1986, "The full length coding sequence of rat liver androsterone UDP–glucuronyltransferase cDNA and comparison with other members of this gene family", Nucl. Acids Res. 14:779–795.

Joziasse, 1992, "Mammalian glycosyltransferases: genomic organization and protein structure", Glycobiology 2:271–277.

Joziasse et al., 1989, "Bovine α1→3–galactosyltransferase: isolation and characterization of a cDNA clone", J. Biol. Chem. 264:14290–14297.

Kimura and Owens, 1987, "Mouse UDP glucuronosyltransferase", Eur. J. Biochem. 168:515–521.

Kukowska–Latallo et al., 1990, "A cloned human cDNA determines expression of a mouse stage–specific embryonic antigen and the Lewis blood group α(1,3/1,4)fucosyltransferase", Genes and Devel. 4:1288–1303.

Larsen et al., 1990, "Molecular cloning, sequence, and expression of a human GDP–L–fucose:β–D–galactoside 2–α–L–fucosyltransferase cDNA that can form the H blood group antigen", Proc. Natl. Acad. Sci. USA 87:6674–6678.

Larsen et al., 1989, "Isolation of a cDNA encoding a murine UDPgalactose:β–D–galactosyl–1, 4–N–acetyl–D–glucosaminide α–1,3–galactosyltransferase: expression cloning by gene transfer", Proc. Natl. Acad. Sci. USA 86:8227–8231.

Lowe, 1991, "Molecular cloning, expression and uses of mammalian glycosyltransferases", Semin. Cell Biol.2:289–307.

Mackenzie, 1986, "Rat liver UDP–glucuronosyltransferase", J. Biol. Chem. 261:14112–14117.

Masri et al., 1988, "Identification of the full–length coding sequence for human galactosyltransferase (β–N–acetylglucosaminide:β1,4–galactosyltransferase)", Biochem. Biophys. Res. Commun. 157:657–663.

Nakazawa et al., 1988, "Cloning and sequencing of a full–length cDNA of mouse N–acetylglucosamine (β1–4)galactosyltransferase", J. Biochem. 104:165–168.

Narimatsu et al., 1986, "Cloning and sequencing of cDNA of bovine N–acetylglucosamine (β1–4)galactosyltransferase", Proc. Natl. Acad. Sci. USA 83:4720–4724.

Nishikawa et al., 1992, "Purification, cDNA cloning and expression of UDP–N–acetylglucosamine:β–D–mannoside β–1,4N–acetylglucosaminyltransferase III from rat kidney", J. Biol. Chem. 267:18199–18204.

Nitschke et al., 1990, "Molecular cloning, nucleotide sequence and expression in *Escherichia coli* of the β–cyclodextrin glycosyltransferase gene from *Bacillus circulans* strain No. 8", Appl. Microbiol. Biotechnol. 33:542–546.

Rajan et al., 1989, "A cloned human DNA restriction fragment determines expression of a GDP–L–fucose: β–D–galactoside 2α–L–fucosyltransferase in transfected cells", J. Biol. Chem 264:11158–11167.

Sarkar et al., 1991, "Molecular cloning and expression of cDNA encoding the enzyme that controls conversion of high–mannose to hybrid complex N–glycans: UDP–N–acetylglucosamine:α–3–D–mannoside β–1, 2–N–acetylglucosaminyltransferase I", Proc. Natl. Acad. Sci. USA 88:234–238.

Shaper et al., 1988, "Characterization of the full length cDNA for murine β–1,4–galactosyltransferase", J. Biol. Chem. 263:10420–10428.

Shaper et al., 1986, "Bovine galactosyltransferase: identification of a clone by direct immunological screening of a cDNA expression library", Proc. Natl. Acad. Sci. USA 83:1573–1577.

Weinstein et al., 1987, "Primary structure of β–galactoside α 2,6–sialyltransferase. Conversion of membrane–bound enzyme to soluble forms by cleavage of the $NH_2$–terminal signal anchor", J. Biol. Chem. 262:17735–17743.

Wen et al., "Primary structure of galβ1,3(4)glcNAc α2,3–sialyltransferase determined by mass spectrometry sequence analysis and molecular cloning", J. Biol. Chem. 267:21011–21019.

Weston et al., 1992, "Molecular cloning of a fourth member of a human α(1,3)fucosyltransferase gene family", J. Biol. Chem. 267:24575–24584.

Weston et al., 1992, "Isolation of a novel human α(1,3)fucosyltransferase gene and molecular comparison to the human Lewis blood group α(1,3/1,4)fucosyltransferase gene", J. Biol. Chem. 267:4152–4160.

Gillespie et al., 1992, "Cloning and expression of the galβ1,3galNAc α2,3–sialyltransferase", J. Biol. Chem. 267:21004–21010.

Livingston and Paulson, 1993, "Polymerase chain reaction cloning of a developmentally regulated member of the sialyltransferase gene family", J. Biol. Chem. 268:11504–11507.

Charbit et al., 1991. "Permissive Sites and Topology of an Outer Membrane Protein with a Reporter Epitope", J. Bacteriol. 173:262–275.

* cited by examiner

METHOD OF SYNTHESIZING SACCHARIDE COMPOSITIONS

This application is a continuation application of application Ser. No. 08/664,882 filed Jun. 17, 1996, U.S. Pat. No. 5,879,912, which is a continuation of application Ser. No. 08/091,372 filed Jul. 15, 1993 now abandoned, each of which is incorporated by reference herein in its entirety.

BACKGROUND OF THE INVENTION

1. Field of the Invention

This invention relates to methods of preparing saccharide compositions such as, for example, oligosaccharides, polysaccharides, glycolipids, and glycoproteins.

2. Discussion of the Background

The term "carbohydrate" embraces a wide variety of chemical compounds having the general formula $(CH_2O)_n$, such as monosaccharides, disaccharides, oligosaccharides and polysaccharides. Oligosaccharides are chains composed of saccharide units, which are alternatively known as sugars. These saccharide units can be arranged in any order and the linkage between the two saccharide units can occur in any of approximately 10 different ways. As a result, the number of different possible stereoisomeric oligosaccharide chains is enormous.

Of all the biological polymer families, oligosaccharides and polysaccharides have been the least well studied, due in part to the difficulty of sequencing and synthesizing their often complex sugar chain. Although the synthesis of oligonucleotides and polypeptides are well developed, there is currently no generally applicable synthetic technique for synthesizing oligosaccharides.

Numerous classical techniques for the theoretical synthesis of carbohydrates have been developed, but these techniques suffer the difficulty of requiring selective protection and deprotection, and, to date, have only provided very limited results. Organic synthesis of oligosaccharides is further hampered by the lability of many glycosidic bonds, difficulties in achieving regioselective sugar coupling, and generally low synthetic yield. These difficulties, together with the difficulties of isolating and purifying carbohydrates and of analyzing their structure, has made this area of chemistry a very demanding one.

Intensive research efforts have been devoted to carbohydrates and molecules comprising carbohydrate fragments, such as glycolipids and glycoproteins. Research interest in these moieties has been largely due to the recognition that interaction between proteins and carbohydrates are involved in a wide array of biological recognition events, including fertilization, molecular targeting, intracellular recognition, and viral, bacterial, and fungal pathogenesis. It is now widely appreciated that the oligosaccharide portions of glycoproteins and glycolipids mediate the recognition between cells and cells, between cells and ligands, between cells and extracellular matrix, and between cells and pathogens.

These recognition phenomena can likely be inhibited by oligosaccharides which have the same sugar sequence and stereochemistry found on the active portion of a glycoprotein or glycolipid involved in cell recognition. The oligosaccharides are believed to compete with the glycoproteins and glycolipids for binding sites on the receptor proteins. For example, the disaccharide galactosyl β 1-4 N-acetylglucosamine is believed to be one component of the glycoprotein which interacts with receptors in the plasma membrane of liver cells. To the extent that they compete with potentially harmful moieties for cellular binding sites, oligosaccharides and other saccharide compositions have the potential to open new horizons in pharmacology, diagnosis and therapeutics.

There has been relatively little effort to test oligosaccharides as therapeutic agents for humans or animal diseases however, as methods for the synthesis of oligosaccharides have been unavailable as noted above. Limited types of small oligosaccharides can be custom-synthesized by organic chemical methods, but the cost of such compounds is typically prohibitively high. In addition, it is very difficult to synthesize oligosaccharides stereospecifically and the addition of some sugars, such as sialic acid and fucose, has not been effectively accomplished because of the extreme lability of their bonds. Improved, generally applicable methods for oligosaccharide synthesis are thereby desired for the production of large amounts of widely varying oligosaccharides for therapeutic purposes.

For certain applications, enzymes have been targeted for use in organic synthesis as one alternative to more traditional techniques. For example, enzymes have been used as catalysts in organic synthesis, where the value of synthetic enzymatic reactions in such areas as reaction rate acceleration and stereoselectivity has been demonstrated. Additionally, techniques are now available for the low cost production of some enzymes and for alteration of their properties.

Glycosyltransferases catalyze the addition of activated sugars (donor NDP-sugars), in a step wise fashion, to a protein, glycoprotein, lipid or glycolipid or to the non-reducing end of a growing oligosaccharide. N-linked glycoproteins are synthesized via a transferase and a lipid-linked oligosaccharide donor [Dol-PP-NAG$_2$Glc$_3$Mang$_9$] in an en block transfer followed by trimming of the core. In this case the nature of the "core" saccharide is somewhat different from subsequent attachments. A very large number of glycosyltransferases appears to be necessary to synthesize carbohydrates. Each donor NDP-sugar residue requires a distinct class of glycosyltransferases and each of the more-than-100 glycosyltransferases identified to date appears to catalyze the formation of a unique glycosidic linkage. To date, the exact details of the specificity of the glycosyltransferases are not known. It is not clear for example what sequence of carbohydrates is recognized by most of these enzymes.

Glycosyltransferases have been found in soluble form in many vertebrate body fluids, but they are generally in membrane-bound form when associated with cells. Many of the membrane-bound enzymes studied thus far are considered to be intrinsic proteins; that is, they are not released from the membranes by sonication and require detergents for solubilization. Before 1971, glycosyltransferase activities were generally thought to be localized in the Golgi-retractions and endoplasmic reticulum of cells, since that was the finding in rat liver. Since then, surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition. (Roth, *Molecular Approaches to Supracellular Phenomena*, 1990).

Cells expressing cell surface glycosyltransferase activity have previously been identified. As a source of sialyltransferase activity Cerven has reported such activity on the surface of intact Ehrlich ascites cells that were passed in Swiss albino mice. Bernacki has also measured endogenous sialyltransferase activity on intact leukemic L1210 cells. For a review of cell surface glycosyltransferase activity, see Pierce et al., *International Review of Cytolocy*, 65: 1–44 (1980).

In other cases it has been recognized that some glycosyltransferases, particularly those which are membrane bound require the presence of an additional protein to exhibit transferase activity (Xelleher.D. J. et al, *Cell*, 69: 55–65, 1992)).

Further, methods have been developed to alter the glycosyltransferases expressed by cells. Larsen et al., *Proc. Natl. Acad. Sci. U.S.A.*, 86: 8227–8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:β-D-galactosyl-1,4-N-acetyl-D-glucosaminide α-1,3-galactosyltransferase was transfected into COS-1 cells. The transfected cells were then cultured and assayed for a 1–3 galactosyltransferase activity.

Paulson et al., U.S. Pat. No. 5,032,519, discloses a method of producing secretable glycosyltransferases. According to this meth i, eukaryotic cells express a genetically altered soluble form of a glycosyltransferase in addition to the endogenous Golgi-bound form of the enzyme. However, the Paulson et al method is limited only to eukaryotic cell systems.

Francisco et al, *Proc. Natl. Acad. Sci. U.S.A.*, 89: 2713–2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning. Such bacterial tripartite fusions may not be suitable for industrial purposes because of the extreme burden on a cell to produce the long fusion protein thereby reducing cellular efficiency and growth. Production of the fusion protein construct is believed to be-counter productive.

Despite the advancements in modulation of bound and unbound glycosyltransferases, the applications of such modified organisms has been very limited. In fact, these transformed cells have only been used to transgenically produce glycosylated proteins where only the non-glycosylated proteins have previously been available.

Since extracellular glycosyltransferases appear on the cell surface, it is now possible to utilize the activity of these glycosyltransferases in a synthetic method.

SUMMARY OF THE INVENTION

Accordingly, one object of this invention is to provide a novel method of synthesizing saccharide compositions, including oligosaccharides, using cell surface bound glycosyltransferases.

Another object of the present invention is to provide a bioreactor suitable for synthesizing said saccharide compositions in accordance with the invention comprising at least one cell culture (if more than one, then each expressing a different glycosyltransferase) and means for isolating the saccharide composition.

Another object of the present invention is to provide a bioreactor suitable for synthesizing said saccharide compositions in accordance with the invention comprising at least one cell culture, expressing a glycosyltransferase along with the conjugate donor saccharide.

The inventor has now discovered that the above objects of the invention, and other objects which will become apparent from the description of the invention given hereinbelow, are satisfied by a method for the glycosyltransferase catalyzed preparation of a saccharide composition by serially bonding preselected saccharide units to an acceptor moiety in which (i) an acceptor moiety is contacted with at least one donor saccharide in the presence of at least one cell surface-bound glycosyltransferase-specific for catalyzing the coupling of the acceptor moiety with the donor saccharide. The acceptor moiety is a carbohydrate, a glycoprotein, or a glycolipid. When the acceptor moiety is a protein or lipid, the resulting product is an O-linked glycoprotein or an O-linked glycolipid. The saccharide composition product is then isolated, and optionally further purified.

DETAILED DESCRIPTION OF THE PREFERRED EMBODIMENTS

As employed in this text, the term "saccharide composition" includes any chemical moiety having a saccharide unit within its structure. Sugars, carbohydrates, saccharides, monosaccharides, oligosaccharides, polysaccharides, glycoproteins, and glycolipids are examples of saccharide compositions. Mixtures and solutions comprising such entities are also saccharide compositions.

In accordance with the present invention, an acceptor moiety is provided which is capable of being covalently bound to a preselected saccharide unit. Representative acceptor moieties include proteins, glycoproteins, lipids, glycolipids, and carbohydrates such as monosaccharides, disaccharides, oligosaccharides and/or polysaccharides. It will be appreciated that acceptor moieties are preferred to the extent that they are present as a structural component of a saccharide composition of interest. It will be appreciated that when proteins and lipids are the acceptor, an O-linked glycoprotein or O-linked glycolipid will result. In order to form N-linked glycoproteins, the core saccharide unit must first be attached. For example, in preparing a saccharide composition such as N-acetylneuraminyl α2–3 galactosyl β1–4 N-acetylglucosamine, the acceptor moieties are N-acetylglucosamine and galactosyl β1–4 N-acetylglucosamine. It will likewise be appreciated that where an acceptor moiety is terminated by a saccharide unit, subsequent saccharide units will typically be covalently bound to the non-reducing terminus of the terminal saccharide.

The donor saccharide is provided in the form of a nucleoside mono- or diphosphate sugar. In mammalian systems, 8 monosaccharides are activated in this form to provide the building blocks for most oligosaccharides: UDP-Glc, UDP-GlcUA, UDP-GlcNAc, UDP-Gal, UDP-GalNAc, GDP-Man, GDP-Fuc and CMP-NeuAc.

In its simplest form, the method of the present invention provides for bringing together an acceptor and at least one donor saccharide in the presence of at least one cell culture. When more than one cell culture is used, each may preferably bear a different cell surface bound glycosyltransferase capable of catalyzing the coupling of the acceptor and one donor saccharide as well as the acceptor-donor saccharide complex with the second donor saccharide. A single donor saccharide may be used where the trisaccharide is the result of binding the acceptor with two units of the same donor saccharide. The cell culture is allowed to grow and continually produce cells bearing membrane-bound glycosyltransferase. In the presence of an acceptor and two donor saccharides, a bioreactor for producing a trisaccharide is provided.

The cells used according to the present process are cultures of a cell which expresses, on the cell surface, the glycosyltransferase of interest which is capable of catalyzing the reaction between the acceptor and donor moieties. While cell surface glycosyltransferases occur naturally, it is also possible to transfect cells with genes to express a glycosyltranferase of interest.

Transfected cells may be obtained by methods known to those of ordinary skill in the art. For example, to obtain transfected cells, DNA, including cDNA, that contain the natural or modified sequences, that encode the catalytic and transmembrane regions of the glycosyltransferase, are transferred into a cell which naturally lacks expression of the glycosyltransferase of interest. Cells that already have cell surface expression of the glycosyltransferase of interest may also be transfected with the desired cDNA in order to obtain cells that have an even higher specific transferase activity on their surface.

In many cases DNA (including cDNA) encoding glycosyltransferase genes have already been isolated and sequenced. A gene that encodes lactose synthetase has been reported for the bovine enzyme (Narimatsu et al, *Proc. Natl. Acad. Sci. USA*, 83: 4720–24 (1986) and Shaver et al, *Proc. Natl. Acad. Sci. USA*, 83: 1573–77 (1986)) and a human enzyme (Appert et al, *Biochem. Biophvs. Res. Comm.*, 139: 163–68 (1986)). Other glycosyltransferase genes which have been reported are two sialyltransferase (Weinstein et al, *J. Biol. Chem.*, 262: 17735–43 (1987); Wen et al., *J. Biol. Chem.*, 267: 21011–19 (1992)), rat liver glucuronyltransferase (Jackson and Burcheli, *Nuc. Acids Res.*, 14: 779–95 (1986); Mackenzie, J. *Biol. Chem.*, 261: 14112–17 (1986)), a mouse glucuronyltransferase (Kimura and Owens, *Eur. J. Biochem.*, 168: 515–21 (1987)), a human glucuronyltransferase (Jackson, *Biochem. J.*, 242: 581–88 (1987)), a human N-acetylgalactosaminyltransferase (Nagata et al., *J. Biol. Chem.*, 267: 12082–89 (1992)), a mouse galactosyltransferase (Larsen et al., *Proc. Natl. Acad. Sci. U.S.A.*, 86: 8227–31 (1989)), a rabbit N-acetylglucosaminyltransferase I (Sarkar-et al., *Proc. Natl. Acad. Sci. U.S.A.*, 88: 234–38 (1991)), a rat N-acetylglucosaminyltransferase III (Nishikawa et al., *J. Biol. Chem.*, 267: 18199–204 (1992)), a number of human fucosyltransferases (Larsen et al., *Proc. Natl. Acad. Sci. U.S.A.*, 87: 6674–78 (1990); Kukowska-Latallo et al., *Genes and Development* 4: 1288–303 (1990); Weston et al., *J. Biol. Chem.*, 267: 4152–60 (1992)), a human N-acetylglucosaminyltransferase (Berhuizen and Fukuda, *Proc. Natl. Acad. Sci. U.S.A.*, 89: 9326–30 (1992)), and a bovine N-acetylgalactosaminyltransferase (Homa et al., *J. Biol. Chem.*, 268: 12609–16 (1993)).

For glycosyltransferases for which a gene (DNA or cDNA) is not readily available, the following approach may be used to obtain the DNA(S) encoding the glycosyltransferase(s) of interest. Generally, in the synthesis of a saccharide composition in accordance with the invention, a preselected saccharide unit is first enzymatically attached to an initial acceptor moiety, i.e., a protein, a glycoprotein, a lipid, a glycolipid, or a carbohydrate starting material. This is followed by enzymatically attaching preselected saccharide units to the product obtained in a sequential fashion thereby forming the saccharide composition.

With the attachment of each preselected saccharide unit, one obtains an intermediate product. As described in greater detail in the inventor's U.S. Pat. No. 5,180,674, in the invention described therein the starting material of the synthesis (i.e., the protein, glycoprotein, lipid, glycolipid or carbohydrate) and each intermediate product formed in the synthesis can be advantageously used to obtain, for each corresponding step of the synthesis, a glycosyltransferase specific to catalyze the attachment of the next intermediate product in the synthesis of the target saccharide composition.

Thus, the glycosyltransferase needed for any given step is isolated with the intermediate product (the acceptor moiety) and used to attach to the acceptor moiety the next saccharide unit necessary for construction of the target carbohydrate molecule. This process may be repeated, with each iteration (time) yielding the particular glycosyltransferase required to attach the next saccharide unit onto the growing molecule being isolated, until the target carbohydrate molecule is obtained. In this manner, glycosyltransferases specific for any particular acceptor moiety and capable of transferring a preselected saccharide unit to the acceptor moiety may be isolated and accordingly all of the enzymes for a given synthesis may be obtained.

Alternatively, the peptide sequence may be obtained from a glycosyltransferase that has been purified by conventional methods known to those of ordinary skill in the art. Synthetic degenerate oligonucleotides derived from the peptide sequence can be used to screen lambda, cosmid, or YAC libraries and thus isolate cDNA or genomic clones for the various glycosyltransferases. The polymerase chain reaction (PCR) method can also be used to clone glycosyltransferases using the synthetic oligonucleotide probes described above. Finally, expression cloning which has been used successfully to isolate a number of glycosyltransferases (Larsen st al., *Proc. Natl. Acad. Sci. U.S.A.*, 87: 6674–78 (1990); Nacata et al.,*J. Biol. Chem.*, 267: 12082–89 (1992)) can also be used to obtain cDNAs encoding other glycoslytransferases.

Each requisite enzyme needed to synthesize an oligosaccharide of interest may be identified and obtained by contacting the acceptor moiety with a mixture suspected to contain a plurality of glycosyltransferases, including the glycosyltransferase of interest, under conditions effective to bind the acceptor moiety and the glycosyltransferase specific for the acceptor moiety. The mixture suspected to contain the glycosyltransferase of interest may be identified as follows. For the most common glycosidic linkages, the glycosyltransferase activities have been described in publications. This is largely true for compounds like milk oligosaccharides, or the carbohydrate moieties of typical (i.e., prevalent) glycoproteins and glycolipids. For less well described linkages, one may first look to the tissue, organ, on foodstuff organism, in which the linkage is found. Generally, if the linkage is found in a particular source, the enzyme that made the linkage is also present in the source.

If one is presented only with a saccharide structure, and not a source, one can then test examples of organisms that are likely to contain such a saccharide structure (relying on publications of relevant structures) using the most sensitive screening assay available. For example, if the target compound contained iduronic acid, N-acetylgalactosamine and N-acetylglucosamine, one would test vertebrate connective tissue. If the target compound contain abequose, one would test bacteria and plants for the presence of the appropriate glycosyltransferase.

Various assays for detecting glycosyltransferases which can be used in accordance with the invention have been published. The following are illustrative. Furukawa et al, *Biochem. J.*, 227:573–582 (1985) describe a borate-impregnated paper electrophoresis assay and a fluorescence assay (FIG. 6) developed by the inventor. Roth et al, *Exp'l Cell Research* 143:217–225 (1983) describe application of the borate assay to glucuronyl transferases, previously assayed calorimetrically. Benau et al, *J. Histochem. Cytochem.*, 38:(1):23–30 (1990) describe a histochemical assay based on the reduction, by NADH, of diazonium salts.

Once a source for the glycosyltransferase of interest has been found, the source is homogenized. The enzyme is purified from the homogenate by affinity chromatography using the acceptor moiety as the affinity ligand. That is, the homogenate is passed over a solid matrix having immobilized thereon the acceptor moiety under conditions which cause the glycosyltransferase to bind to the acceptor moiety.

Monitoring for acceptor-bound enzyme can be carried out as follows. The cell homogenate is passed over the immobilized acceptor moiety. This may be achieved, for example, by passing the cell homogenate over a column charged with immobilized acceptor moiety. The column is then washed and the amount of protein which passes through the column charged with immobilized acceptor moiety is monitored. When no more protein is detected, an aqueous salt solution or solution of a suitable sugar donor eluant is passed through the column to elute the enzyme. The eluant obtained is then assayed for the presence of glycosyltransferase(s). The assays which can be used are noted above, i.e., the methods described by Furukawa et al., Roth et al and Benau et al.

If no binding of the enzyme to the acceptor moiety occurs (i.e., the assay of the eluate fails to reveal the presence of glycosyltransferase(s) therein), then it can be concluded that the mixture did not contain an enzyme specific for the particular acceptor. Other mixtures of, for example, animal and/or plant cell homogenates are then contacted with the acceptor moiety until enzyme binding is observed.

When the acceptor moiety is bound by an enzyme, the species are separated. For example, the solid support matrix having the glycosyltransferase bound thereto is washed. This is followed by an elution step in which the glycosyltransferase is desorbed from the solid support matrix and collected. As known, the absorbed glycosyltransferase may be eluted, for example, by passing an aqueous salt (e.g. NaCl) solution over the solid support matrix.

In a preferred embodiment, the acceptor and the candidate enzyme are again contacted, this time in the presence of a donor moiety which comprises the saccharide unit desired to be transferred to the acceptor moiety. If such contacting results in the transfer of the saccharide unit to the acceptor, the enzyme is a glycosyltransferase useful in the practice of this invention.

It will be appreciated that once the glycosyltransferase is identified and isolated, it can be sequenced, DNA sequence encoding the enzyme obtained and/or replicated by techniques well-known to those skilled in the art. For example, obtaining a DNA sequence encoding the enzyme may be accomplished by recombinant techniques involving the isolation of genetic material coding for the glycosyltransferase and the preparation of an immortal cell line capable of amplifying the amount of DNA encoding the glycosyltransferase. This may be accomplished by determining the amino acid sequence of the glycosyltransferase (using known techniques) to a degree sufficient to enable isolation of a DNA sequence encoding the enzyme using a DNA or an RNA probe, preferably using degenerate probes.

In accordance with the present invention the DNA (including cDNA) encoding for glycosyltransferase genes can be introduced into a host cell in either native or engineered form in both procaryotic or eukaryotic cells using known techniques as follows.

In the case of procaryotes, the signal and transmembrane sequences of the glycosyltransferase are replaced by a bacterial signal sequence, capable of effecting localization of the fusion protein to the outer membrane. Suitable signal sequences include, but are not limited to those from the major *E.coli* lipoprotein Lpp and lam B. In addition, membrane spanning regions from Omp A, Omp C, Omp F or Pho E can be used in a tripartite fusion protein to direct proper insertion of the fusion protein into the outer membrane. Any procaryotic cells can be used in accordance with the present invention including but not limited to *E. coli*, Bacillus sp., and Pseudomonas sp. as representative examples.

In another embodiment, the native transmembrane domain of the glycosyltranferase is replaced by the transmembrane domain of a bacterial outer membrane protein. In this embodiment, the glycosyltransferase signal sequence and the bacterial transmembrane region act in concert to anchor the glycosyltransferase to the bacterial outer cell membrane. Any outer membrane bound protein is suitable for this use including but not limited to Omp A, Omp C, and Omp F, Lpp, and Lam B so long as the transmembrane structure is known to such extent that one can determine the position, in the linear sequence, an extracellular loop occurs in the protein. The catalytic portion of the glycosyltransferase should be fused to an extracellular loop in the bacterial transmembrane region in order to insure proper orientation of the fusion protein on the outer membrane surface and not in the cytoplasm or periplasm of the cell. Insertion into such a loop region without description of the proper transmembrane folding has been previously reported (Charbit et al., *J. Bacteriology*, 173: 262–275 (1991); Francisco, et al., *Proc. Natl. Acad. Sci. U.S.A.*, 89: 2713–2717 (1992)).

The present invention is also applicable for use with eukaryotic cells resulting in cell surface expression of glycosyltransferases in known culturable eucaryotic cells including but not limited to yeast cells, insect cells, chinese hamster ovary cells (CHO cells), mouse L cells, mouse A9 cells, baby hamster kidney cells, C127 cells, and PC8 cells.

Paulson et al. (U.S. Pat. No. 5,032,519, incorporated herein by reference) describe a method of engineering glycosyltranferases to result in secretion of a soluble form of the enzyme. The patentees describe the removal of the hydrophobic transmembrane anchor region of the glycosyltransferase which results in secretion of the protein in a soluble form. In the present invention the native transmembrane region of the glycosyltransferase is modified to allow the recombinant protein to be localized to the extracellular surface of the plasma membrane of the cell.

In a preferred embodiment of the present invention, the transmembrane domain of the glycosyltransferase is replaced by the transmembrane domain of a plasma membrane protein. The transmembrane domain of any resident plasma membrane protein will be appropriate for this purpose. The transmembrane portions of the M6 P/IGF-II receptor, LDL receptor or the transferrin receptor are representative examples. Further, a short cytoplasmic peptide in addition to the transmembrane portion would give improved anchoring into a plasma membrane. The cytoplasmic tails of any of the three previously mentioned receptor proteins will suffice if their internalization signals have been inactivated by site-directed mutagenesis (Johnson et al., *Proc. Natl. Acad. Sci. U.S.A.*, 87: 10010–10014 (1990); Canfield et al.,

*J. Biol. Chem.*, 266: 5682–5688 (1991)). Inactivation of the internalization signal can be achieved by modification of the four amino acid sequence tyr-X-X-Y, where X is any amino acid and Y is either leu, isoleu or val. The internalization signal is inactivated by conversion of the tyrosine to an alanine and Y to an alanine.

In another preferred embodiment the Golgi retention signal of the glycosyltransferase is disrupted by site-directed mutagenesis. This approach mutates the few amino acids responsible for localizing the glycosyltransferase to the Golgi compartment. The resultant glycosyltransferase is transported to the plasma membrane where it becomes anchored via its modified transmembrane sequences. Substitution of isoleucine residues for the native amino acids in the transmembrane region of the β-1,4-galactosyltransferase has been shown to preferentially localize the enzyme to the plasma membrane instead of the Golgi apparatus (Masibay et al., *J. Biol. Chem.*, 268: 9908–19916 (1993)). While not wishing to be bound to any particular theory, it is believed that substitution of the isoleucine residues, increases the hydrophobicity of the transmembrane sequence, resulting in the preferential localization of the enzyme in the plasma membrane.

Any of the well known procedures, to those of ordinary skill in the art, for introducing foreign DNA sequences into a host cell may be used with the present invention. Suitable vectors for transporting the DNA into the cell include but are not limited to plasmid vectors, viral vectors and any of the other well known methods for introducing cloned genomic DNA, cDNA, synthetic DNA, semi-synthetic DNA and any other foreign genetic materials into a host cell.

Suitable procaryotic vectors include but are not limited to pBR322, pMB9, pUC, lambda bacteriophage, m13 bacteriophage, and Blue script®.

Suitable eukaryotic vectors include but are not limited to PMSG, pAV009/A+, PMTO10/A+, pMAM neo-5, bacculovirus, pDSVE, YIP5, YRP17, YEP.

It will be clear to one of ordinary skill in the art which vector or promoter system should be used depending on which cell type is used for a host cell.

Preferably, the cell culture only expresses-the cell surface glycosyltransferase of interest.

Suitable cells may be identified by incubating the cells believed to express the cell surface glycosyltransferase activity of interest with the appropriate acceptor and radiolabeled donor sugar moiety. At the end of the incubation period, the glycosylated product is separated from the unused radioactive substrate. The synthesis of the appropriate acceptor-donor condensate is then evidence of the presence of the glycosyltransferase activity of interest on the cell surface.

In this fashion, an entire library of cell cultures may be identified which express, on their cell surface, a specific glycosyltransferase. For example, a cell culture which expresses N-acetylglucosaminyl transferase on the cell surface may be identified and stored. Likewise a cell culture which expresses a galactosyltransferase may also be identified and stored.

Once a library of suitable glycosyltransferases has been identified, it is then possible to select the specific glycosyltransferases needed to synthesize an oligosaccharide of interest.

For example, in order to synthesize lacto-N-neotetraose, an oligosaccharide found in human milk of the structure β-D-Gal 1–4 β-D-GlcNAc 1–3 β-D-Gal 1–4 D-Glc, it is necessary to provide two cell cultures which provide the requisite two glycosyltransferases necessary to form the β-Gal 1–4 GlcNAc bond, and the β-GlcNAc 1–3 Gal bond. In the presence of these two cell cultures and UDP-GlcNAc, and UDP-Gal, β-D-Gal 1–4 D-Glc(i.e. lactose) is converted into lacto-N-neotetraose.

By assembling the cell cultures, acceptor and source of donor sugars, it is now possible to design a bioreactor to synthesize any oligosaccharide composition containing naturally occurring glycosidic linkages. The bioreactor would mimic the results of a conventional bioreactor, in that cultured cells would produce a biological product of interest, however, in the present process, the product of interest can be determined at will. The bioreactor may contain any number of different cell cultures depending on the number of glycosyltransferases needed to prepare the oligosaccharide of interest. Particularly the bioreactor may contain from one, two, three or four different cell cultures, each expressing a different glycosyltransferase on the cell surface. The separate cell cultures will provide the same function as a single cell, however since the cell cultures and donor sugars may be selected, the resulting product may be predetermined.

Suitable cells which express glycosyltransferase activity may be transfected procaryotic or eukaryotic cells. Preferably, transfected yeast cells which express the glycosyltransferases of interest are used.

The present invention may also be practiced with a multiplicity of cells expressing different glycosyltransferases in the same manner as described above, such that a cell surface glycosyltransferase and conjugate donor saccharides are contacted with a suitable acceptor to form an oligosaccharide.

In this fashion, any oligosaccharide of interest may be formed simply by bringing together the appropriate cells expressing the requisite cell surface glycosyltransferases and the necessary acceptor and donor saccharides. It is now possible to generate a "designer" bioreactor through selection of cell cultures and donor saccharide units.

In a preferred embodiment, a bioreactor containing a cell culture that expresses a given conjugate sugar nucleotide donor, due to transfection of cDNAs that encode the enzymes necessary for synthesis of this saccharide donor, is allowed to interact with another bioreactor containing a cell culture which has surface expression of the appropriate glycosyltransferase for the conjugate sugar nucleotide. Suitable cells are identified by including the appropriate radiolabeled acceptor moiety in the culture medium. At the end of the incubation period, the glycosylated product is separated from the unused radioactive acceptor. Formation of the radiolabeled product is evidence that a cell culture expressing the conjugate saccharide donor and a cultured cell expressing the glycosyltransferase on its surface are both present. It is also possible that the cell culture which has surface expression of the appropriate glycosyltransferase and the cell culture which expresses a given conjugate sugar nucleotide donor interact in a single bioreactor.

In another preferred embodiment, the same cell culture has both surface expression of a glycosyltransferase and expresses the conjugate donor saccharide. Suitable cells are identified by incubating the cell believed to express the cell surface glycosyltransferase and conjugate moiety. At the end of the incubation period, the glycosylated product is separated from the unused radioactive acceptor. The reaction of the radioactive acceptor is evidence of the presence of a surface glycosyltransferase and conjugate donor saccharide in the same cell culture. The glycosyltransferase activity is then identified by characterization of the acceptor-donor saccharide composition.

Through identification of cell cultures which express both a glycosyltransferase and conjugate donor saccharide, the efficiency of any bioreactor containing this cell culture is greatly enhanced due to obviating the need to separately supply the donor saccharide.

The bioreactor according to the present invention may be any conventionally used cell culture reactor. A suitable reactor will provide a means for maintaining a stable suitable temperature, a supply of essential cell nutrients, and means for mixing the contents of the reactor.

According to the present process, cells may be cultured continuously, or in batches according to standard techniques.

Cells may be cultured in a modified batch process through continuous phasing of the nutrient environment (U.S. Pat. No. 3,419,703)

The saccharide compositions which can be prepared in accordance with this invention are believed to find wide utility in diagnostics, therapeutics, and pharmacological applications. Once the sugar sequence of a desired target saccharide composition has been determined by conventional methods, a retrosynthetic analysis is generally performed to determine an appropriate synthetic scheme for the saccharide composition. Such a synthetic scheme preferably identifies the particular donor moieties, acceptor moieties, and glycosyltransferase necessary to yield the desired saccharide composition.

These and other features of the invention will become apparent in the course of the following descriptions of exemplary embodiments which are given for illustration of the invention and are not intended to be limiting thereof.

EXAMPLE 1

Synthesis of Lacto-N-neotetraose

To a cell culture apparatus containing a suitable reaction culture medium is added two cell cultures, each of which express a different glycosyltransferase. One cell culture expresses a glycosyltransferase necessary to produce the Gal 1–4 GlcNAc bond. A second cell culture provides a glycosyltransferase necessary to form the GlcNAc 1–3 Gal bond. The reaction medium consists of water and suitable nutrients to support the growth of the cell culture. Into this cell culture apparatus is also provided, one eq. of UDP-GlcNAc, and one eq. of UDP-Gal. A molar equivalent of lactose is then added to the reaction medium. The reactor is brought to a temperature of 35° C. and reacted for 28 hours. The cell cultures are then separated by filtration and the supernatant liquid is purified by chromatography to yield lacto-N-neotetraose.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method, for the glycosyltransferase-catalyzed preparation of a preselected saccharide composition having a defined sequence of saccharide subunits by serially bonding saccharide units to an acceptor moiety comprising:

(a) contacting said acceptor moiety with a first saccharide unit in the presence of a first cell surface genetically engineered to express a first cell surface-bound glycosyltransferase specific for catalyzing the linkage of said acceptor moiety with said first saccharide unit to form a first saccharide composition having a defined sequence of saccharide subunits; and (b) contacting said first saccharide composition with a second saccharide unit in the presence of a second cell surface genetically engineered to express a second cell surface-bound glycosyltransferase specific for catalyzing the linkage of said first saccharide composition with said second saccharide unit, wherein said second saccharide unit is different from said first saccharide unit, to form a preselected serially bound second saccharide composition having a defined sequence of saccharide subunits:

wherein the first and second cell surface-bound glycosyltransferases are each selected from the group consisting of a galactosyltransferase, a sialyltransferase, a fucosyltransferase, an N-acetylgalactosaminyltransferase, an N-acetylglucosaminyltransferase, and a glucuronyltransferase.

2. The method of claim 1, further comprising the step of isolating said preselected serially bound second saccharide composition.

3. The method of claim 1, wherein said first or second saccharide unit is an activated sugar.

4. The method of claim 1, wherein said first or second saccharide unit is selected from the group consisting of UDP-Glc, UDP-GlcUA, UDP-GlcNAc, UDP-Gal, UDP-GalNAc, GDP-Man, GDP-Fuc and CMP-NeuAc.

5. The method of claim 1, wherein one of said first or second genetically engineered cell surfaces is prokaryotic.

6. The method of claim 1, wherein said acceptor moiety is a carbohydrate, a glycoprotein or a glycolipid.

7. The method of claim 6, wherein said carbohydrate is selected from the group consisting of a monosaccharide, a disaccharide, an oligosaccharide and a polysaccharide.

8. The method of claim 5, wherein said prokaryotic cell surface is genetically engineered to express a cell surface-bound prokaryotic glycosyltransferase.

9. The method of claim 8, wherein said cell surface-bound prokaryotic glycosyltransferase is a β1–4 glycosyltransferase.

10. The method of claim 8, wherein said cell surface-bound prokaryotic glycosyltransferase is a β1–3 glycosyltransferase.

11. The method of claim 8, wherein said prokaryotic cell surface is genetically engineered to express a cell surface-bound prokaryotic glycosyltransferase by transfection with a cDNA containing DNA vector comprising DNA encoding a bacterial signal sequence, a transmembrane domain of a bacterial outer membrane protein and a prokaryotic glycosyltransferase.

12. The method of claim 11, wherein said bacterial signal sequence and bacterial transmembrane domain correspond to DNA encoding a signal sequence and transmembrane domain of a protein selected from the group consisting of E. coli outer membrane protein A (Omp A), E. coli outer membrane protein C (Omp C), E. coli outer membrane protein F (Omp F), major E. coli lipoprotein (Lpp) and E. coli outer membrane protein maltoprotein (Lam B).

13. The method of claim 1, wherein said first saccharide unit or said second saccharide unit is provided by a cell.

14. The method of claim 5, wherein said prokaryotic cell surface is genetically engineered to express a cell surface-bound eukaryotic glycosyltransferase.

15. The method of claim 14, wherein said prokaryotic cell surface is genetically engineered to express a cell surface-bound eukaryotic glycosyltransferase by transfection with a cDNA containing DNA vector comprising DNA encoding a bacterial signal sequence and a eukaryotic glycosyltransferase, wherein the DNA encoding the hydrophobic membrane region of the glycosyltransferase is replaced with DNA encoding a transmembrane domain of a bacterial outer membrane protein.

16. The method of claim 15, wherein said bacterial signal sequence and bacterial transmembrane domain encoding DNA correspond to DNA encoding a signal sequence and transmembrane domain of a protein selected from the group consisting of Omp A, Omp C, Omp F, Lpp and Lam B.

17. The method of claim 1, wherein one of said first or second genetically engineered cell surfaces is eukaryotic.

18. The method of claim 17, wherein said acceptor moiety is a carbohydrate, a glycoprotein or a glycolipid.

19. The method of claim 18, wherein the carbohydrate is selected from the group consisting of a monosaccharide, a disaccharide, an oligosaccharide and a polysaccharide.

20. The method of claim 17, wherein said eukaryotic cell surface is a yeast cell surface.

21. The method of claim 17, wherein said eukaryotic cell surface is genetically engineered to express a cell surface-bound eukaryotic glycosyltransferase.

22. The method of claim 21, wherein said cell surface-bound eukaryotic glycosyltransferase is a β1–4 glycosyltransferase.

23. The method of claim 21, wherein said cell surface-bound eukaryotic glycosyltransferase is a β1–3 glycosyltransferase.

24. The method of claim 21, wherein said eukaryotic cell surface is genetically engineered to express a cell surface-bound eukaryotic glycosyltransferase by transfection with a cDNA containing DNA vector comprising DNA encoding a eukaryotic glycosyltransferase, wherein the DNA encoding the hydrophobic membrane region of the glycosyltransferase is replaced with DNA encoding the hydrophobic membrane region of a eukaryotic cell surface protein.

25. The method of claim 24, wherein said replaced DNA encodes the hydrophobic membrane region of a eukaryotic cell surface protein selected from the group consisting of mannose 6 phosphate/insulin-like growth factor II receptor, low density lipoprotein receptor and transferrin receptor.

26. The method of claim 17, wherein said eukaryotic cell surface is genetically engineered to express a cell surface-bound prokaryotic glycosyltransferase.

27. The method of claim 26, wherein said eukaryotic cell surface is genetically engineered to express a surface-bound prokaryotic glycosyltransferase by transfection with a cDNA containing DNA vector comprising DNA encoding a eukaryotic signal sequence, a hydrophobic membrane region of a eukaryotic cell surface protein, and a prokaryotic glycosyltransferase.

28. The method of claim 27, wherein said eukaryotic signal sequence and hydrophobic membrane region encoding DNA correspond to DNA encoding a signal sequence and hydrophobic membrane region of a protein selected from the group consisting of mannose 6 phosphate/insulin-like growth factor II receptor, low density lipoprotein receptor and transferrin receptor.

* * * * *